(12) United States Patent
Mackool

(10) Patent No.: US 7,014,629 B2
(45) Date of Patent: Mar. 21, 2006

(54) TAPERED INFUSION SLEEVE PORTAL

(75) Inventor: Richard J. Mackool, Astoria, NY (US)

(73) Assignee: Alcon, Inc, Hünenberg (CH)

( * ) Notice: Subject to any disclaimer, the term of this patent is extended or adjusted under 35 U.S.C. 154(b) by 352 days.

(21) Appl. No.: 10/319,302

(22) Filed: Dec. 13, 2002

(65) Prior Publication Data

US 2004/0153026 A1 Aug. 5, 2004

(51) Int. Cl.
*A61M 5/32* (2006.01)

(52) U.S. Cl. ...................................................... 604/274
(58) Field of Classification Search .................. 604/22, 604/264, 265, 271, 272, 274, 35, 43, 27, 604/239
See application file for complete search history.

(56) References Cited

U.S. PATENT DOCUMENTS

| | | | | |
|---|---|---|---|---|
| 2,634,726 A | * | 4/1953 | Hanson | 604/274 |
| 2,697,438 A | * | 12/1954 | Hickey | 604/274 |
| 2,748,769 A | * | 6/1956 | Huber | 604/272 |
| 4,014,333 A | * | 3/1977 | McIntyre | 604/43 |
| 4,634,420 A | * | 1/1987 | Spinosa et al. | 604/22 |
| 4,689,040 A | * | 8/1987 | Thompson | 604/22 |
| 4,705,500 A | * | 11/1987 | Reimels et al. | 604/35 |
| 4,787,889 A | * | 11/1988 | Steppe et al. | 604/22 |
| 4,808,170 A | * | 2/1989 | Thornton et al. | 604/274 |
| 4,846,172 A | * | 7/1989 | Berlin | 606/4 |
| 4,983,160 A | * | 1/1991 | Steppe et al. | 604/22 |
| 5,112,339 A | * | 5/1992 | Zelman | 606/107 |
| 5,133,159 A | | 7/1992 | Nelson | |
| 5,193,159 A | | 7/1992 | Nelson | |
| 5,154,696 A | * | 10/1992 | Shearing | 604/22 |
| 5,284,476 A | * | 2/1994 | Koch | 604/274 |
| 5,286,256 A | * | 2/1994 | Mackool | 604/22 |
| 5,919,157 A | | 7/1999 | Strukel | |
| 6,299,591 B1 | | 10/2001 | Banko | |

OTHER PUBLICATIONS

Excerpts from www.alconlabs.com/us/aj/products, 1998–2002.

* cited by examiner

*Primary Examiner*—Sharon Kennedy
(74) *Attorney, Agent, or Firm*—Gibbons, Del Deo, Dolan, Griffinger & Vecchione

(57) ABSTRACT

A tapered infusion sleeve that has an orifice whose exterior margin is either rounded off, beveled, tapered, curved inclined or otherwise forms an angle with an adjacent exterior of the sleeve that is other than ninety degrees and other than substantially ninety degrees. As a result, the exterior margin is less likely to become caught or ensnared when being passed through an incision opening with a surgical instrument.

18 Claims, 1 Drawing Sheet

TAPERED INFUSION SLEEVE PORTAL

BACKGROUND OF THE INVENTION

1. Field of the Invention

The present invention relates to an infusion portal on the side of an infusion sleeve of a surgical instrument.

2. Discussion of Related Art

Phacoemulsification instruments and irrigation/aspiration instruments are known that have infusion portals in their malleable infusion sleeves. Alcon Surgical Laboratories commercializes such a phacoemulsification system under the name SERIES 20000® LEGACY®. The phacoemulsification system is commercialized with a handpiece and malleable infusion sleeves with infusion portals. The sleeves partially shroud needles, such as those commercialized under the tradename Mackool System® such as the MACKOOL MICROTIP or the MACKOOL FLARED ABS, which are named after the present inventor.

The infusion portal in the malleable infusion sleeve is typically formed by punching out that portion of the sleeve that is to form the infusion portal, thereby leaving a hole or orifice. Conventionally, the wall of the infusion port is at a 90° angle to the entry of the hole or orifice.

The present inventor, who has performed thousands of cataract operations, has made some observations. When inserting the needle and sleeve through an incision, the edges of the portal tend to become caught on the edges of the adjacent incision. This requires the surgeon to press more forcefully in an attempt to insert the needle and sleeve to a desired location. Trauma to the surrounding tissues may result as a result of trying to break the portal free of being caught on the edges of the adjacent incision.

Indeed, by twisting and turning the handpiece (basically oscillating it as it is advanced), the tip can eventually be introduced. Greater effort is required and some surgeons (fearful that the manipulation causes trauma) simply make the incision larger than optimum so that tip insertion is easier. A larger than necessary incision results in fluid leakage from the eye during the procedure, with resultant greater difficulty in controlling eye pressure during the surgery, potential collapse of the eye with trauma to ocular structures such as the cornea, iris, posterior lens capsule, etc. In addition, a larger incision results in greater total fluid flow through the eye, and this fact alone cause greater trauma.

On the other hand, pushing and oscillating the instrument through a tight incision can cause the edge of the portals to damage the cornea, particularly the inner lining of the cornea known as Descemet's membrane and the attached corneal endothelial cells, which can be stripped from the portion of the cornea above them (the corneal stroma) to which Descemet's membrane is normally attached. This is an extremely serious complication, well-known to occur as a result of the insertion of blunt instruments through corneal incisions, and this may so seriously damage the cornea that a corneal transplant may become necessary to restore sight. I have personally seen this occur as a result of sharp edged portals on several occasions.

No matter how skillful the surgeon, the current design requires greater force in order to accomplish insertion unless the incision is made larger than would otherwise be necessary to permit insertion of the tip or the portals are made smaller than optimally desirable. If the latter is done, the portals may be placed more toward the tip of the tapered infusion sleeve, where its diameter is less. Thus the portal may avoid contact with the sides of the incision during insertion.

However, smaller than optimal portals restrict the rate at which fluid can enter the eye, thereby limiting the rate at which the pump can run as it removes the cataract (i.e. a lower aspiration flow rate must be used), as well as limiting the suction level that can be applied to the cataract to remove it. Using less suction/vacuum generally results in a less efficient and slower procedure, and also requires that more ultrasonic energy be used to remove the cataract. It is therefore desirable to have little or no fluid leakage from the incision during the period when the tip is in the eye, and to construct the infusion sleeve with portals large enough so that they do not create any limitation to infusion flow into the eye.

SUMMARY OF THE INVENTION

One aspect of the present invention resides in configuring at least a portion of an external margin of a portal of an infusion sleeve of a surgical instrument and an adjacent portion of an exterior of the infusion sleeve of the surgical instrument to be other than perpendicular to each other and other than substantially perpendicular to each other. For instance, the portion of the external margin may have a configuration that is either rounded off, beveled, inclined, tapered or curved. A surgeon using the present invention may apply a substantially steady and constant force on the surgical instrument to insert its tip with the infusion sleeve through an incision without edges of the portal becoming caught or ensnared by the incision. Trauma to the surrounding tissues that might otherwise occur as a result of trying to break the portal free of being caught on the edges of the incision is avoided.

BRIEF DESCRIPTION OF THE DRAWING

For a better understanding of the present invention, reference is made to the following description and accompanying drawings, while the scope of the invention is set forth in the appended claims:

DETAILED DESCRIPTION OF THE INVENTION

Figure 1:
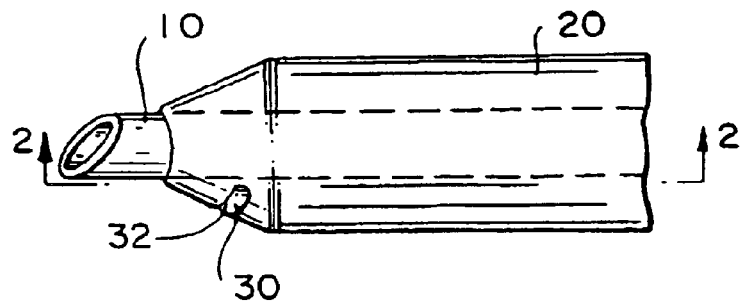
FIG. 1 is an elevation side view of a surgical instrument's needle and sleeve with infusion port in accordance with the prior art.
Figure 2:
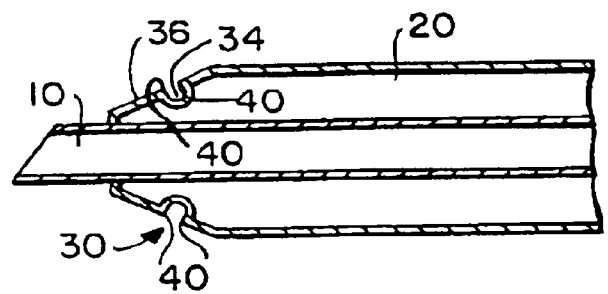
FIG. 2 is a cross section of the surgical instrument's needle and sleeve with infusion port of FIG. 1.

Turning to FIGS. 1 and 2, a conventional needle 10 and malleable infusion sleeve 20 are depicted. The malleable infusion sleeve 20 has one or more infusion portals 30 that includes at least one orifice 32 whose wall 34 terminates at the external surface 36 of the infusion sleeve 20 to form a sharp edge 40. That is, the wall of each of the infusion portals 30 is essentially is at a 90° angle to the external surface 36. The infusion portal is arranged closer to the distal end of the sleeve than to the proximal end for delivering infusion fluid to an operating site adjacent the tip of the needle 10.

I have designed infusion sleeves for Alcon Surgical Laboratories that have little or no fluid leakage from the incision during the period when the tip is in the eye and have constructed the infusion sleeve with portals large enough so that they do not create any limitation to infusion flow into the eye (they call them "high infusion sleeves"). To accomplish this, the edges of the external margin of the portals needed to be rounded off. This is desirable, even if small portals are placed on the tapering portion of the infusion sleeve, because it is still possible for them to traumatize the cornea during tip insertion, although less likely than with larger portals.

Figure 3:
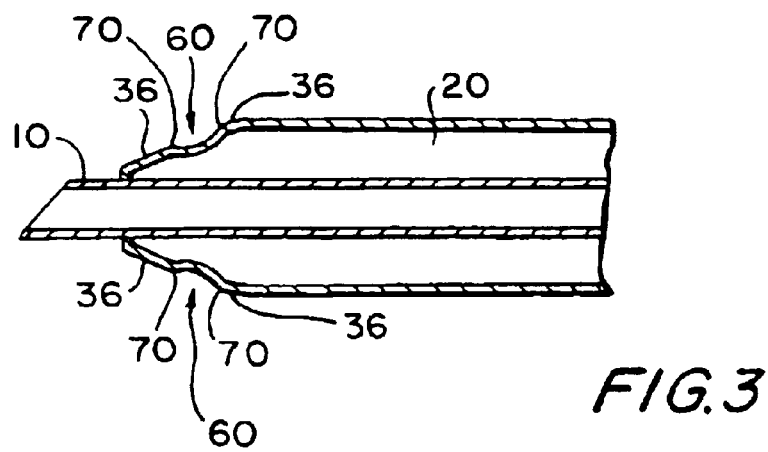
FIG. 3. is a cross section of the surgical instrument's needle and sleeve with infusion port in accordance with my invention.

Turning to FIG. 3, the needle 10 and the malleable infusion sleeve 20 with one or more infusion portals 60 are shown in accordance with my invention. Each external margin 70 of the portals 60 is rounded off, inclined, curved, tapered or beveled to provide a more gradual transition to the external surface 36 of the sleeve 20 and thus is less sharp than is the case for the infusion portals 30 of FIG. 1. The external margin 70 and the external surface 36 of the infusion sleeve 20 are arranged other than perpendicular to each other and other than substantially perpendicular to each other. The external margin 70 forms at least a portion of at least one orifice of at least one of the portals 60.

This rounding off, inclining, tapering or beveling of the external margin 70 of the portals 60 may be effected in any conventional manner, whether done simultaneously with the forming of the portals 60 (such as at the time of the punch-out by employing a punch that converges as it presses from the exterior surface of the sleeve to penetrate through the sleeve to reach the interior surface of the sleeve) or subsequently with a conventional rounding or beveling tool. Possible mechanisms include lathe cutting or laser ablation.

This rounding, tapering or beveling off may be done over an entirety of the circumference of the external margin 70 of the portals 60 or on any portion of the external margin 70. The distal portion of the portals 60 (that is, that part of the portals 60 which enter the eye last) should be rounded, tapered or beveled off because if left as a sharp margin, the distal portion is likely to encounter the tissues while passing through the incision to become caught or ensnared and thus result in the unwanted trauma condition. The infusion sleeve 20 preferably has a tapering portion that tapers to the distal end or preferably has reduced diameter portion at a distal end that is of a smaller diameter than the proximal end. The portal is preferably located in this tapering portion or reduced diameter portion.

The needle 10 is of conventional construction and has an aspiration inlet port on one side of the needle and an internal flow passage. A generator of ultrasonic energy is used to apply ultrasonic energy to vibrate or oscillate the needle. An aspiration suction force is applied to the internal flow passage to aspirate tissue into the aspiration inlet port. The sleeve 20 surrounds at least a portion of the needle and is malleable so as to compress against a wall at the opening of an incision as the sleeve passes through to conform to the shape of the opening. Infusion fluid is administered through a space between the needle 10 and an interior surface of the sleeve 20 and flows through an outlet port to reach the operating site.

As discussed, an infusion sleeve of a surgical instrument is provided that has an orifice whose exterior margin is either rounded off, beveled, tapered, inclined, curved or otherwise forms an angle with an adjacent exterior of the sleeve that is other than ninety degrees and other than substantially ninety degrees. The external margin of the portal may taper or converge inwardly toward the interior of the infusion sleeve from the exterior as it traverses the thickness of the infusion sleeve. As a result, the exterior margin is less likely to become caught or ensnared when being passed through an incision opening.

As a consequence, a surgeon using the present invention may apply a substantially steady and constant force on the surgical instrument to insert the tip through an incision without edges of the portals becoming caught or ensnared by the adjacent incision. Trauma to the surrounding tissues that might otherwise occur as a result of trying to break the portal free of being caught on the edges of the adjacent incision is avoided.

Infusion sleeves are used for different types of surgical instruments. For instance, they are not only for ultrasonic vibrating instruments, such as phacoemulsification instruments, but also for non-ultrasonic vibrating instruments that are commonly referred to as irrigation/aspiration instruments. These irrigation/aspiration instruments remove portions of the cataract from the eye (generally softer portions) that do not require the use of a vibrating ultrasonic generator to impose a vibrating force on the needle. The sleeves on these instruments have portals that suffer from the same problem as the phacoemulsification instrument infusion sleeves currently have, and the solution as set forth in this patent application applies as well to them. That is, at least a portion of the external margin and an adjacent portion of an exterior of the infusion sleeve of the irrigation/aspiration instruments need to be configured and arranged to be other than perpendicular to each other and other than substantially perpendicular to each other.

While the foregoing description and drawings represent the preferred embodiments of the present invention, it will be understood that various changes and modifications may be made without departing from the spirit and scope of the present invention.

What is claimed is:

1. A surgical instrument, comprising a needle having an aspiration inlet port and an internal flow passage arranged so that as an aspiration suction force is applied to the internal flow passage, aspirated tissue is drawn into the aspiration inlet port to pass through the internal flow passage; an infusion sleeve that is configured and arranged to surround at least a portion of the needle and having proximal and distal ends, the infusion sleeve having an infusion portal that includes an external margin that defines at least a portion of an orifice that is arranged closer to the distal end than to the proximal end of the infusion sleeve, the infusion sleeve and the needle being elongated and being spaced from each other to define a gap between for infusion fluid to flow to reach the orifice and emerge through the infusion portal, at least a portion of the external margin and an adjacent portion of an exterior of the sleeve being configured and arranged to be other than perpendicular to each other and other than substantially perpendicular to each other, the external margin being configured and arranged to traverse a thickness of the infusion sleeve and to converge toward an interior of the infusion sleeve while traversing the thickness.

2. A surgical instrument of claim 1, wherein the portion of the external margin is a distal portion of the external margin, the external margin also having a proximal portion, the distal portion being closer to the distal end of the sleeve than is the proximal portion of the external margin, the proximal portion of the external margin being closer to the proximal end of the sleeve than is the distal portion of the external margin.

3. A surgical instrument of claim 1, wherein the portion of the external margin constitutes an entirety of the external margin.

4. A surgical instrument of claim 1, characterized in that the portion of the external margin has a configuration that is selected from a group consisting of rounded off, beveled, inclined, tapered and curved.

5. A surgical instrument of claim 1, wherein the infusion sleeve has a reduced diameter portion that terminates at the distal end and is of a diameter smaller than that of the proximal end, the portal being arranged in the reduced diameter portion.

6. A surgical instrument of claim 5, wherein the reduced diameter portion is formed to taper to the distal end.

7. A surgical instrument of claim 1, wherein the portion of the external margin extends inwardly at an angle from the adjacent portion of the exterior of the sleeve toward an interior of the sleeve to define a contour facing outward that is not sharp.

8. A method of reducing a likelihood of an infusion portal of an infusion sleeve becoming caught on tissue at an incision, the method comprising surrounding at least a portion of a needle with the infusion sleeve, arranging the needle to have an aspiration inlet port and an internal flow passage arranged so that as an aspiration suction force is applied to the internal flow passage, aspirated tissue is drawn into the aspiration inlet port to pass through the internal flow passage; defining a gap between the infusion sleeve and the needle for infusion fluid to flow to reach an orifice and emerge through the infusion portal, defining at least a portion of the orifice by an external margin of the infusion portal, arranging the orifice closer to the distal end of the infusion sleeve than to a proximal end of the infusion sleeve, the infusion sleeve and the needle being elongated, configuring and arranging at least a portion of the external margin of the infusion portal and an adjacent portion of an exterior of the infusion sleeve to be other than perpendicular to each other and other than substantially perpendicular to each other, traversing a thickness of the infusion sleeve by the external margin, converging the external margin toward an interior of the infusion sleeve while traversing the thickness of the infusion sleeve.

9. A method of claim 8, wherein the portion of the external margin is a distal portion of the external margin, the external margin also having a proximal portion, arranging the distal portion closer to the distal end of the sleeve than is the proximal portion of the external margin, and arranging the proximal portion of the external margin closer to the proximal end of the sleeve than is the distal portion of the external margin.

10. A method of claim 8, wherein the portion of the external margin constitutes an entirety of the external margin.

11. A method of claim 8, further comprising configuring the portion of the external margin to have a configuration selected from a group consisting of rounded off, inclined, tapered, curved, and beveled.

12. A method of claim 8, further comprising arranging the portal in a reduced diameter portion of the infusion sleeve, providing the reduced diameter portion of the infusion sleeve with a diameter smaller than that of the proximal end, terminating the reduced diameter portion at the distal end.

13. A method of claim 12, further comprising extending the portion of the external margin inwardly at an angle from the adjacent portion of the exterior of the sleeve toward an interior of the sleeve to define a contour facing outward that is not sharp.

14. A method of claim 8, further comprising extending the portion of the external margin inwardly at an angle from the adjacent portion of the exterior of the sleeve toward an interior of the sleeve to define a contour facing outward that is not sharp.

15. A surgical infusion sleeve having proximal and distal ends, the surgical infusion sleeve having at least one portal that includes at least one orifice arranged closer to the distal end than to the proximal end, the distal end being open, the surgical infusion sleeve having a reduced diameter portion that terminates at the distal end and is smaller in diameter than the proximal end, the at least one portal being arranged in the reduced diameter portion and having an external margin that defines the orifice, at least a portion of the external margin and an adjacent portion of an exterior of the sleeve being configured and arranged to be other than perpendicular to each other and other than substantially perpendicular to each other.

16. A surgical infusion sleeve of claim 15, wherein the external margin has a configuration selected from a group consisting of rounded off, tapered, beveled, inclined and curved.

17. A surgical infusion sleeve of claim 15, wherein the reduced diameter portion is formed to taper to the distal end.

18. A surgical infusion sleeve of claim 15 wherein the portion of the external margin extends inwardly at an angle from the adjacent portion of the exterior of the sleeve toward an interior of the sleeve to define a contour facing outward that is not sharp.

* * * * *